US008962875B2

(12) United States Patent
Norman et al.

(10) Patent No.: US 8,962,875 B2
(45) Date of Patent: *Feb. 24, 2015

(54) METAL-ENOLATE PRECURSORS FOR DEPOSITING METAL-CONTAINING FILMS

(75) Inventors: John Anthony Thomas Norman, Encinitas, CA (US); Xinjian Lei, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/418,747

(22) Filed: Mar. 13, 2012

(65) Prior Publication Data

US 2013/0066082 A1    Mar. 14, 2013

Related U.S. Application Data

(63) Continuation-in-part of application No. 13/299,448, filed on Nov. 18, 2011, now abandoned.

(60) Provisional application No. 61/418,055, filed on Nov. 30, 2010.

(51) Int. Cl.
*C07F 17/00* (2006.01)
*C23C 16/18* (2006.01)
*C23C 16/40* (2006.01)
*C23C 16/455* (2006.01)

(52) U.S. Cl.
CPC ............... *C07F 17/00* (2013.01); *C23C 16/18* (2013.01); *C23C 16/405* (2013.01); *C23C 16/45553* (2013.01)
USPC ............................... 556/54; 556/56; 427/252

(58) Field of Classification Search
USPC ............ 427/569, 248.1, 250, 252; 556/54, 56
See application file for complete search history.

(56) References Cited

U.S. PATENT DOCUMENTS

| | | | | |
|---|---|---|---|---|
| 2,708,205 | A | * | 5/1955 | Haslam ............................ 526/75 |
| 3,669,825 | A | | 6/1972 | Hall |
| 4,780,337 | A | | 10/1988 | Seyferth et al. |
| 5,389,401 | A | * | 2/1995 | Gordon ..................... 427/255.36 |
| 7,476,420 | B2 | | 1/2009 | Skarp et al. |
| 7,691,984 | B2 | | 4/2010 | Lei et al. |
| 7,723,493 | B2 | | 5/2010 | Lei et al. |
| 2006/0219157 | A1 | | 10/2006 | Rahtu et al. |
| 2007/0248754 | A1 | | 10/2007 | Lei et al. |
| 2008/0072819 | A1 | | 3/2008 | Rahtu et al. |
| 2008/0176162 | A1 | | 7/2008 | Ohmura et al. |
| 2008/0187662 | A1 | | 8/2008 | Wada et al. |
| 2008/0254218 | A1 | | 10/2008 | Lei et al. |
| 2010/0119726 | A1 | | 5/2010 | Lei et al. |
| 2010/0143607 | A1 | | 6/2010 | Lei et al. |

FOREIGN PATENT DOCUMENTS

| | | |
|---|---|---|
| JP | 3-150237 A | 6/1991 |
| JP | 3150237 | 6/1991 |
| JP | 10-182713 | 7/1998 |
| JP | 1129589 A2 | 2/1999 |
| JP | 2004-099524 | 4/2004 |
| JP | 112790 A2 | 5/2007 |
| JP | 2008526577 A | 7/2008 |
| JP | 2009-001896 | 1/2009 |
| JP | 2010177661 A2 | 8/2010 |
| WO | 2006076670 A2 | 7/2006 |
| WO | 2007-106788 A2 | 9/2007 |
| WO | 2007106788 | 9/2007 |
| WO | 2008128141 A | 10/2008 |

OTHER PUBLICATIONS

Roddick et al. Reactions of alkyl and hydride derivatives of permethylzirconene and permethylhanocene with carbon monoxide. Synthesis and reactivity studies of aldehyde complexes of zirconium and hafnium, Chem. Ber. 122 (1989) p. 1579-1587.*
Lang et al. Deposition of metals and metal oxides by means of metal enolates. PATAI's Chemistry of Functional Groups, John Wiley & Sons, Sep. 15, 2010.*
Comins, et al.; "Reioselective Addition of Titanmium Enolates to 1-Acylpyridinium Salts. A Convenient Synthesis of 4-(2-Oxoalkyl)Pyridines"; vol. 25, No. 31; Jan. 1, 1984; pp. 3297-3300.
Reetz, M.T., et al.; "Erythro Selective Aldol Condensation using Titanium Enolates"; vol. 22, No. 47; Jan. 1, 1981; pp. 4691-4694.
Roddick, D.M., et al.; "Reactions of Alkyl and Hydride Derivatives of Permethylzirconocene and Permethylhafnocene with Carbon Monoxide. Synthesis and Reactivity Studies of Aldehyde Complexes of Zirconium and Hafnium"; vol. 122, No. 8; Aug. 1, 1989; pp. 1579-1587.
Curtis, M. David, Simple Synthesis of Enolate Complexes of Titanocene and Zironocene. Molecular of Cp2TI (OC2H3)2, Organometallics, 1984, pp. 1855-1859, vol. 3.
Joung, Ui Gab, Pyridineenolato and Pyridineenamido Complexes of Zirconium, Titanium and Aluminum, Polyhedron 2004, pp. 1587-1594, vol. 23.
Pore, Viljami, Atomic Layer Deposition of Photocatalytic TiO2 Thin Films From Titanium Tetramethoxide and Water, Chemical Vapor Deposition, 2004, pp. 143-148, vol. 10, No. 3.
Shiihara, I., The Organic Chemistry of Titanium, Chemical Reviews, 1960, vol. 61 (1), pp. 1-30, The University of Buffalo, New York.
Comins, et al, Reioselective Addition of Titanimium Enolates to 1-Acylpyridinium Salts, A Convenient Synthesis of 4-(2-Oxoalkyl)Pyridines, vol. 25, No. 31, Jan. 1984, 3297-3300.

(Continued)

Primary Examiner — Joseph Kosack
(74) Attorney, Agent, or Firm — Rosaleen P. Morris-Oskanian

(57) ABSTRACT

Organometallic compounds suitable for use as vapor phase deposition precursors for metal-containing films are provided. Methods of depositing metal-containing films using certain organometallic precursors are also provided. Such metal-containing films are particularly useful in the manufacture of electronic devices.

8 Claims, 6 Drawing Sheets

(56) References Cited

OTHER PUBLICATIONS

Reetz, M.T., et al, Erythro Selective Aldol Condensation using Titanium Enolates, vol. 22, No. 47, Jan. 1, 1981, 4691-4694.

Roddick, D.M., et al, Reactions of Alkyl and Hydride Derivatives of Permethylzirconocene and Permethylhafnocene with Carbon Monoxide, Synthesis and Reactivity Studies of Aldehyde Complexes of Zirconium and Hafnium, vol. 122, No. 8, Aug. 1, 1989, 1579-1587.

Roddick, Dean M. and Bercaw, John E., Reactions of Alkyl and Hydride Derivatives of Permethylzirconocene and Permethylhafnocene with Carbon Monoxide. Synthesis and Reactivity Studies of Aldehyde Complexes of Zirconium and Hafnium, Division of Chemistry and Chemical Engineering, California Institute of Technology, Feb. 23, 1989.

\* cited by examiner

METAL-ENOLATE PRECURSORS FOR DEPOSITING METAL-CONTAINING FILMS

CROSS REFERENCE TO RELATED APPLICATION

The present patent application is a continuation in part of U.S. patent application Ser. No. 13/299,448 filed Nov. 18, 2011, which claimed the priority benefit of prior U.S. Provisional Patent Application Ser. No. 61/418,055 filed Nov. 30, 2010.

BACKGROUND OF THE INVENTION

The present invention relates generally to the field of organometallic compounds. In particular, the present invention relates to the certain organometallic compounds suitable for use in vapor deposition processes such as, but not limited to, atomic layer deposition (ALD) or cyclic chemical vapor deposition (CCVD), that may be used to form, for example, a gate dielectric or capacitor dielectric film in a semiconductor device.

With each generation of metal oxide semiconductor (MOS) integrated circuit (IC), the device dimensions have been continuously scaled down to provide for high-density and high-performance such as high speed and low power consumption requirements. Unfortunately, field effect semiconductor devices produce an output signal that is proportional to the width of the channel, such that scaling reduces their output. This effect has generally been compensated for by decreasing the thickness of gate dielectric, thus bring the gate in closer proximity to the channel and enhancing the field effect which thereby increasing the drive current. Therefore, it has become increasingly important to provide extremely thin reliable and low-defect gate dielectrics for improving device performance.

For decades, a thermal silicon oxide, $SiO_2$, has been mainly used as a gate dielectric because it is stable with the underlying silicon substrate and its fabrication process is relatively simple. However, because the silicon oxide gate dielectric has a relatively low dielectric constant (k), 3.9, further scaling down of silicon oxide gate dielectric thickness has become more and more difficult, especially due to gate-to-channel leakage current through the thin silicon oxide gate dielectric.

This leads to consideration of alternative dielectric materials that can be formed in a thicker layer than silicon oxide but still produce the same or better device performance. This performance can be expressed as "equivalent oxide thickness (EOT)". Although the alternative dielectric material layer may be thicker than a comparative silicon oxide layer, it has the equivalent effect of a much thinner layer of silicon oxide layer.

To this end, high-k metal oxide materials have been proposed as the alternative dielectric materials for gate or capacitor dielectrics. Metal-containing precursors may also be used by themselves or combined with other metal-containing precursors, such as, for example, $Pb(Zr,Ti)O_3$ or $(Ba,Si)(Zr,Ti)O_3$, to make high dielectric constant and/or ferroelectric oxide thin films. Because the dielectric constant of metal oxide materials can be made greater than that of the silicon oxide, a thicker metal oxide layer having a similar EOT can be deposited. As a result, the semiconductor industry requires metal-containing precursors, such as, for example, titanium-containing, zirconium-containing, and hafnium-containing precursors and combinations thereof, to be able to deposit metal-containing films such as, but not limited to, oxide, nitride, silicate or combinations thereof on substrates such as metal nitride or silicon.

Unfortunately, the use of high-k metal oxide materials presents several problems when using traditional substrate materials such as silicon. The silicon can react with the high-k metal oxide or be oxidized during deposition of the high-k metal oxide or subsequent thermal processes, thereby forming an interface layer of silicon oxide. This increases the equivalent oxide thickness, thereby degrading device performance. Further, an interface trap density between the high-k metal oxide layer and the silicon substrate is increased. Thus, the channel mobility of the carriers is reduced. This reduces the on/off current ratio of the MOS transistor, thereby degrading its switching characteristics. Also, the high-k metal oxide layer such as, for example, a hafnium oxide ($HfO_2$) layer or a zirconium oxide ($ZrO_2$) layer has a relatively low crystallization temperature and is thermally unstable. Thus, the metal oxide layer can be easily crystallized during a subsequent thermal annealing process used to distribute the n and p type dopants previously injected into source/drain regions of the device. Crystallization can lead to the formation of grain boundaries in the metal oxide layer through which current can pass thereby degrading the performance of the dielectric oxide as an insulator. Crystallization can also lead an increase in the surface roughness of the metal oxide layer which can also lead to current leakage and dielectric deterioration. Further, the crystallization of the high-k metal oxide layer can also undesirably affect subsequent lithographic alignment processes, due to irregular reflection of the light by the rough surfaces.

In addition to minimizing side reactions with the substrate upon which the metal-containing precursor is deposited, it is also desirable that the metal-containing precursor is thermally stable, and preferably in liquid or low melting solid form. Group 4-containing metal films, for example, are typically deposited using a vapor deposition (e.g., chemical vapor deposition and/or atomic layer deposition) process. It is desirable that these precursors are thermally stable during vapor delivery in order to avoid premature decomposition of the precursor before it reaches the vapor deposition chamber during processing. Premature decomposition of the precursor not only results in undesirable accumulation of side products that will clog fluid flow conduits of the deposition apparatus, but also may cause undesirable variations in composition of the deposited gate dielectric, high dielectric constant and/or ferroelectric metal oxide thin film.

Although metal enolate species have been reported as intermediates and catalytic chemical species used in organic synthesis (Tetrahedron Lett. FIELD Full Journal Title: Tetrahedron Letters 22(47): 4691-4), they have not been isolated as low melting, cleanly evaporating and thermally stable molecules for use in thin film deposition processes, as those described below.

Other prior art includes; US2007/0248754A1, U.S. Ser. No. 11/945,678 filed on Nov. 27, 2007, Applicants' co-pending application U.S. Ser. No. 12/266,806 which was filed on Nov. 11, 2008; Applicants' patents U.S. Pat. No. 7,691,984, and U.S. Pat. No. 7,723,493.

Accordingly, there is a need to develop metal-containing precursors, preferably liquid Group 4 precursors, which exhibit at least one of the following properties: high thermal stability, high chemical reactivity and low melting points.

BRIEF SUMMARY OF THE INVENTION

Described herein are enolate based metal-containing precursors and deposition processes using these precursors for fabricating conformal metal containing films on substrates such as silicon, metal nitride and other metal layers by Atomic Layer Deposition (ALD), Plasma Enhanced Atomic Layer Deposition (PEALD), Atomic Vapor Deposition (AVD), Chemical Vapor Deposition (CVD) and Plasma Enhanced Chemical Vapor Deposition (PECVD).

These metal enolates are shown to be low melting solids that evaporate cleanly to give low residues in Thermo Gravimetric Analysis (TGA) experiments and are, hence, excellent candidate precursor for these deposition techniques. In the TGA technique a sample of precursor is weighed in a microbalance while being subjected to steadily increasing temperature under a steady flow of nitrogen. Clean evaporation with low involatile residue in the hallmark of a good precursor. The residue is preferable <10 wt %, preferably <5%, preferably <2%.

While not wishing to be bound by theory, it is believed that the enolate or dienolate species of this disclosure are optimally substituted with alkyl group in a manner which minimizes intermolecular association, to permit clean vaporization. The alkyl group substitution pattern also can lower the melting point of the metal complex and provide for high reaction rates under ALD or CVD conditions.

This invention also discloses the synthesis of these enolate and dienolate precursors, and their use as ALD or CVD precursors. In addition, while not wishing to be bound by theory, it is believed that the highly novel and rare metal dienolate compounds of this disclosure have additional uses and applications, including, but not limited to, catalysts and as synthetic intermediates in chemical synthesis.

The metal-containing precursors of the present invention comprise an enolate ligand and are represented by the following Formula 1:

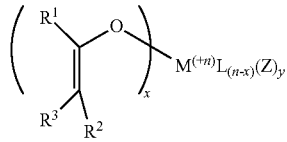

1 wherein, M is a metal with an oxidation state of (n), from +2 to +6, selected from the Lanthanides or Group 3 to Group 16, of the Periodic Table; $R^1$, $R^2$ and $R^3$ are independently H or $C_1$-$C_8$ selected from the group consisting of: methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) is an anionic ligand or a mixture of anionic ligands selected from the group consisting of: alkyl substituted enolate, alkoxy, alkyl amino, dialkylamino (e.g. dimethylamido), diketonate, ketoiminate, diiminate, guanidinate, amidinate, cyclopentadienyl, alkyl substituted cyclopentadienyl, alkoxy substituted cyclopentadienyl, amino substituted cyclopentadienyl, pyrrolyl, alkyl substituted pyrrolyl, alkoxy substituted pyrrolyl, amino substituted pyrrolyl; imidazolate, alkyl substituted imidazolate, alkoxy substituted imidazolate, amino substituted imidazolate, alkoxy substituted imidazolate, pyrazole, alkyl substituted pyrazole, alkoxy substituted pyrazolate, and alkoxy substituted pyrazolate; (L) can also be a dienolate dianion; (Z) is a neutral coordinating ligand, such as an alkylamine, polyalkylamine, ether, polyether, imidazole, pyridine, alkyl substituted pyridine, pyrimidine, alkyl substituted pyrimidine, oxazole, (y)=0 to 4 or 1 to 4, (x)=1 to 6.

Valderaldyl is 1,1-dimethylbutyl. Optionally, (y)=0 to 4.

As an optional feature, $R^1$ or $R^2$ forms a cyclic structure with M, e.g. with $R^2R^3$ for embodiments where L is $C=CR^1$—O— being a dienolate dianion, as shown in Formulae 2, 3, 4 and 5 below. Where $R^1$ or $R^2$ forms a cyclic structure with M, suitably the number of L groups present is (n−2x). Where L is a dienolate dianion, suitably the number of L groups present is (n−x)/2. $R^2R^3C=CR^1$—O— and L may be linked, for example to form a dienolate dianion. $R^1$ and $R^2$ can connect to form a ring. Likewise, $R^1$ or $R^2$ could connect to $R^3$ to form rings.

In certain embodiments of Formula 1, M is Ti, $R^1$ and $R^3$ are tert-butyl and/or $R^2$ is H.

In yet another aspect, the present invention is a compound from Formula 1, wherein (L) is a $C_1$-$C_{10}$ alkoxy group, as represented by structure A1.

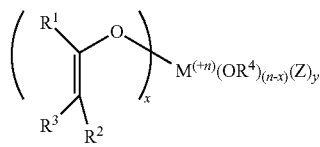

A1 wherein, M is a metal with an oxidation state of (n) ranging from +2 to +6, selected from the Lanthanides or Group 3 to Group 16, of the Periodic Table; $R^1$, $R^2$, and $R^3$ are independently H or $C_1$-$C_6$ selected from the group consisting of: methyl, ethyl, propyl, iso-propyl, butyl, isobutyl, sec-butyl, pentyl, isopentyl, sec pentyl, hexyl, sec-hexyl, tert-butyl, tert-amyl, and 1,1-dimethylbutyl; $R^4$ is selected from the group consisting of methyl, ethyl, propyl, iso-propyl, butyl, isobutyl, sec-butyl, pentyl, isopentyl, sec pentyl, hexyl, sec-hexyl, tert-butyl tert-amyl, and 1,1-dimethylbutyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (y)=1-4; (x)=1 to 6. In certain embodiments of Structure A1, ethoxy and isopropoxy ligands are preferred.

In yet another aspect, the present invention is a compound from Formula 1, wherein (L) is an alkoxy anion, as represented by Structure A2:

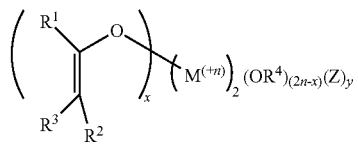

A2 wherein, M is a metal with an oxidation state of (n) ranging from +2 to +6, selected from the Lanthanides or Group 3 to Group 16, of the Periodic Table; $R^1$, $R^2$ and $R^3$ are each independently selected from the group consisting of: H, methyl, ethyl, propyl, iso-propyl, butyl, isobutyl, sec-butyl, pentyl, isopentyl, sec pentyl, hexyl, sec-hexyl, tert-butyl, tert-amyl, and 1,1-dimethylbutyl; $R^4$ is $C_1$-$C_6$ selected from the group consisting of methyl, ethyl, propyl, iso-propyl, butyl, isobutyl, sec-butyl, pentyl, isopentyl, sec pentyl, hexyl, sec-hexyl, tert-butyl tert-amyl, and 1,1-dimethylbutyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (y)=1-4; (x)=1 to 6.

In yet another aspect, the present invention is a compound from Formula 1, wherein (L) is a cyclopentadienyl anion, as represented by Structure B

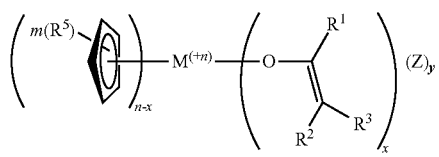

wherein, M is a metal with an oxidation state of (n) ranging from +2 to +6, selected from the Lanthanides or Group 3 to Group 16, of the Periodic Table; $R^1$, $R^2$, $R^3$, and $R^5$ are each independently selected from the group consisting of: H, methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (y)=1-4; (x)=1 to 6; (m)=1 to 5.

In yet another aspect, the present invention is a compound from Formula 1, wherein (L) is a pyrrolyl anion, as represented by Structure C:

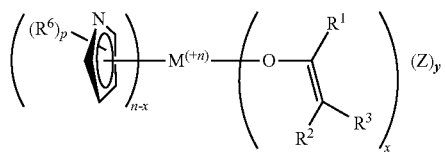

wherein, M is a metal with an oxidation state of (n) ranging from +2 to +6, selected from the Lanthanides or Group 3 to Group 16, of the Periodic Table; $R^1$, $R^2$, $R^3$ and $R^6$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (y)=1 to 4; (x)=1 to 6; (p)=1 to 4.

In yet another aspect, the present invention is a compound from Formula 1, wherein (L) is an imidazolate anion, as represented by Structure D:

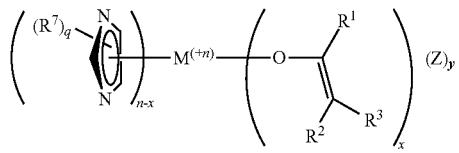

wherein, M is a metal with an oxidation state of (n) ranging from +2 to +6, selected from the Lanthanides or Group 3 to Group 16, of the Periodic Table; $R^1$, $R^2$, $R^3$ and W are each independently selected from the group consisting of: H, methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (y)=1 to 4; (x)=1 to 6; (q)=1, 2 or 3.

In yet another aspect, the present invention is a compound from formula 1, wherein (L) is a pyrazolate anion, as represented by Structure E:

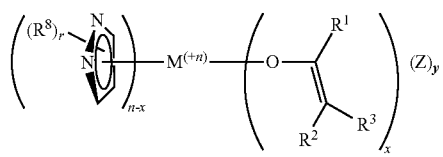

wherein M is a metal with an oxidation state of (n) ranging from +2 to +6 selected from the Lanthanides or Group 3 to Group 16 of the Periodic Table; (n) ranges from +2 to +6; $R^1$, $R^2$, $R^3$ and $R^8$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, 1,1-dimethylbutyl and tert-amyl; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (x)=1 to 4; r=1, 2 or 3; (y)=1 to 4.

In yet another aspect, the present invention provides a compound represented by Formula 2:

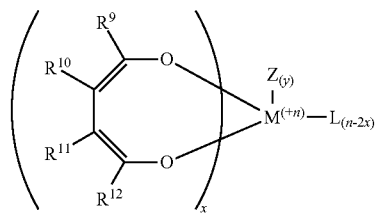

wherein M is a metal with an oxidation state of (n) ranging from +2 to +6 selected from the Lanthanides or Group 3 to Group 16 of the Periodic Table; $R^9$, $R^{10}$, $R^{11}$ and $R^{12}$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) represents an anion or anions selected from the group consisting of: alkyl substituted enolate anion, alkoxy, guanidinate, amidinate, dialkylamide, diketonate, ketoiminate, diiminate, cyclopentadienyl, alkyl substituted cyclopentadienyl, alkoxysubstituted cyclopentadienyl, aminosubstituted cyclopentadienyl, pyrrolyl, alkyl substituted pyrrolyl, alkoxysubstituted pyrrolyl, aminosubstituted pyrrolyl, alkyl substituted imidazolate, and alkoxysubstituted imidazolate; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (x)=1 to 3; (y)=1 to 4. In one preferred embodiment of this aspect of the invention, Z is dimethylamine.

In yet another aspect, the present invention is a compound represented by Formula 3:

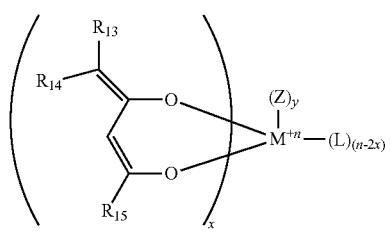

3 wherein M is a metal with an oxidation state of (n) ranging from +2 to +6 selected from the Lanthanides or Group 3 to Group 16 of the Periodic Table; $R^{13}$, $R^{14}$ and $R^{15}$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) represents an anion or anions selected from the group consisting of: alkyl substituted enolate anion, alkoxy, guanidinate, amidinate, dialkylamide, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; alkyl substituted imidazolate, and alkoxysubstituted imidazolate; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (x)=1 to 3; (y)=1 to 4.

In yet another aspect, the present invention is a compound represented by Structure 4:

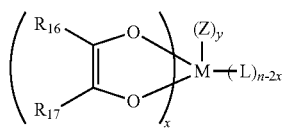

4 wherein M is a metal with an oxidation state of (n) ranging from +2 to +6 selected from the Lanthanides or Group 3 to Group 16 of the Periodic Table; $R^{16}$ and $R^{17}$ are each independently selected from the group consisting of: H, methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) represents an anion or anions selected from the group consisting of: alkyl substituted enolate anion, alkoxy, guanidinate, amidinate, dialkylamide, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; alkyl substituted imidazolate, and alkoxysubstituted imidazolate; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (x)=1 to 3; (y)=1 to 4.

In yet another aspect, the present invention is a compound represented by Formula 5:

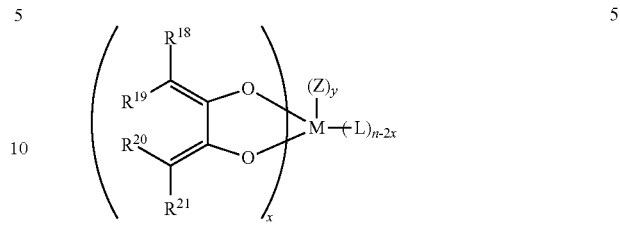

5 wherein M is a metal with an oxidation state of (n) ranging from +2 to +6 selected from the Lanthanides or Group 3 to Group 16 of the Periodic Table; $R^{18}$, $R^{19}$, $R^{20}$ and $R^{21}$ are each independently selected from the group consisting of: H, methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) represents an anion or anions selected from the group consisting of: alkyl substituted enolate anion, alkoxy, guanidinate, amidinate, dialkylamide, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; alkyl substituted imidazolate, and alkoxysubstituted imidazolate; (Z) is a neutral coordinating ligand selected from the group consisting of an alkyl amine, polyalkylamine, ether, polyether, imidazole, pyridine, alkyl substituted pyridine, pyrimidine, alkyl substituted pyrimidine, and oxazole; (x)=1 to 3; (y)=1 to 4.

In yet another aspect, the present invention provides a method for forming a metal-containing film by utilizing these enolate and dienolate precursors of this disclosure in solutions for spin-on thin film growth.

In yet another aspect, the present invention provides a method for forming a metal-containing film by utilizing these volatile enolate and dienolate precursors as CVD or cyclic CVD precursors whereby the precursor and a reagent are flowed simultaneously into the reaction chamber to deposit a film onto a heated substrate. This can be run continuously or in a pulsed mode.

In yet another aspect, the present invention provides a method for forming a metal-containing film by ALD, the method comprises the steps of: a. introducing a metal-containing precursor of this disclosure in a vapor state into a reaction chamber and chemisorbing the metal-containing precursor onto a substrate which is heated; b. purging away the unreacted metal-containing precursor; c. introducing an oxidizing source such as, but limited to, oxygen, ozone, nitrous oxide or water onto the heated substrate to react with the adsorbed metal-containing precursor; and d. purging away the unreacted oxidizing source. This sequence of cycles is then repeated to build up the metal oxide film thickness.

In a preferred embodiment of this invention, the precursor is a liquid or a solid with melting point below 100° C.

While not wishing to be bound by theory, advantages of these precursors are that they are low melting point solids or liquid and thermally stable, as demonstrated by their TGA performance, and are reactive under ALD or CVD conditions to allow the deposition of highly conformal metal oxide films by atomic layer deposition or cyclic chemical vapor deposition at temperatures ranging from 100° C. to 600° C. The novel enolate and dienolate precursors of this disclosure can also be utilized to deposit one or more metal elements contained in mixed metal oxide films such as, but not limited to strontium titanate (STO) or barium strontium titanate (BST).

BRIEF DESCRIPTION OF SEVERAL VIEWS OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
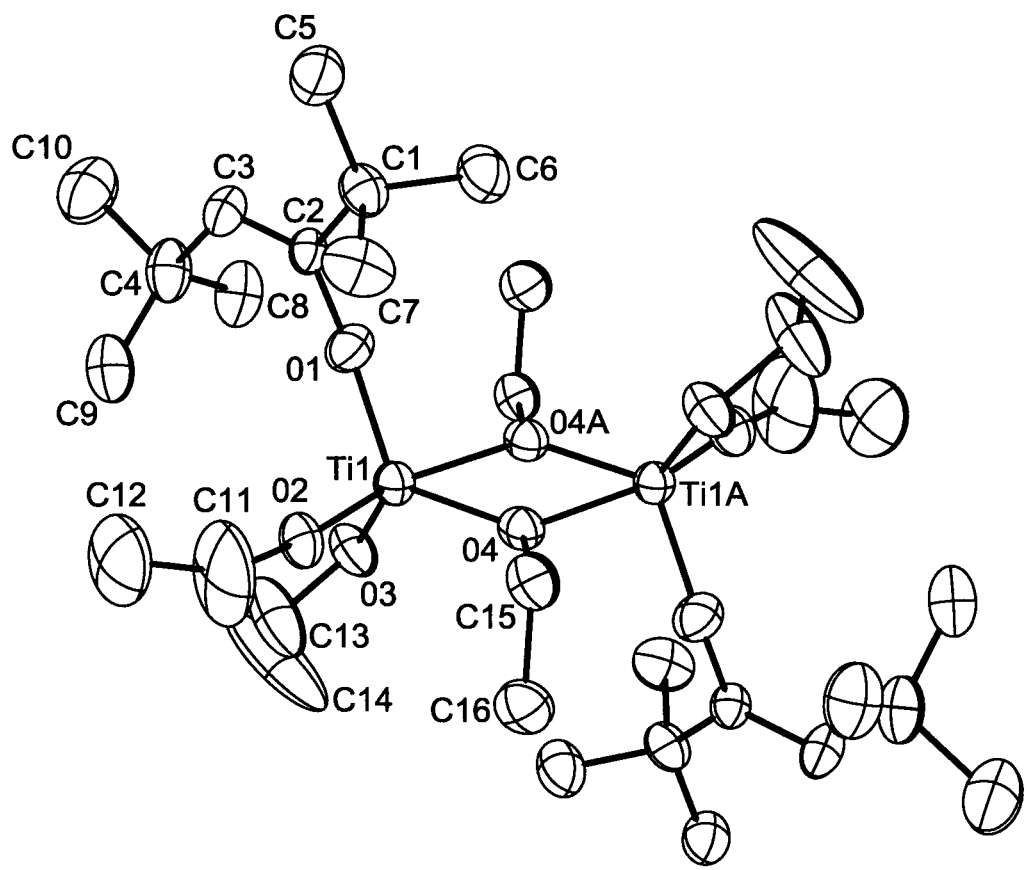
FIG. 1 is a schematic representation of a crystal structure of di-titanium bis(2,2,5,5-tetramethylhex-3-en-3-olato)hexa (ethoxy), characterized by X-ray single crystal diffraction.

Disclosed herein are liquid or low-melting point solid metal-enolate complexes comprising an enolate moiety that are suitable, for example, as precursors in chemical vapor deposition processes. Novel dienolate metal complexes are also described. The complexes and compositions are useful for fabricating metal containing films on substrates such as silicon, metal nitride, metal oxide, metal oxynitride, metal silicate, and other metal containing layers via chemical vapor deposition (CVD), cyclical chemical vapor deposition (CCVD), or atomic layer deposition (ALD) or Atomic Vapor Deposition (AVD) processes. The deposited metal films have applications ranging from computer chips, optical device, magnetic information storage, to metallic catalyst coated on a supporting material.

Also disclosed herein are methods for preparing these precursors, as well as their use in vapor deposition processes, particularly CVD or ALD deposition processes.

The metal-containing precursors of the present invention comprise an enolate complex and are represented by Formula 1 and dienolate complexes represented by Formulae 2, 3, 4 and 5. In one embodiment of the present invention, M is selected from the group consisting of a lanthanide metal and groups 3 to 16 of the periodic table. In another embodiment M is selected from lanthanide, Ti, Zr, Hf, V, Nb, Ta, Cr, Mo, W, and Mn. In certain embodiments of the present invention, M is a Group 4 metal. In one particular embodiment, M is Ti. Exemplary examples of these precursors include but are not limited to bis(2,2,5,5-tetramethylhex-3-en-3-olato)hexa (ethoxy)di-titanium, bis(2,2,5,5-tetramethylhex-3-en-3-olato)bis(iso-propoxy)titanium, tris(2,2,5,5-tetramethylhex-3-en-3-olato)(dimethylamido)titanium. and bis(2,2,7,7-tetramethylocta-3,5-diene-3,6-diolato)bis(dimethylamino) titanium.

The metal-containing precursors of the present invention comprising a dienolate ligand are represented by Formulae 2, 3, 4 and 5. In one embodiment of the present invention, M is selected from the group consisting of a lanthanide metal and groups 3 to 16 of the periodic table. In another embodiment M is selected from lanthanide, Ti, Zr, Hf, V, Nb, Ta, Cr, Mo, W, and Mn. In a preferred embodiment of the present invention, M is a Group 4 metal. In a most preferred embodiment of the present invention, M is Ti. An exemplary complex is bis(2,2, 7,7-tetramethylocta-3,5-diene-3,6-diolato)bis(dimethylamino)titanium.

In a preferred embodiment of the present invention, the groups $R^1$, $R^2$ and $R^3$ of the enolate anion of Formula 1 are comprised of a $C_1$-$C_6$ alkyl group such as methyl, ethyl, propyl, isopropyl, butyl, tert-butyl, isobutyl, secbutyl, pentyl, cyclopentyl, hexyl, or cyclohexyl. In another embodiment of the present invention, $R^1$, $R^2$ or $R^3$ are each independently selected from the group consisting of: hydrogen, methyl, ethyl, iso-propyl, n-propyl, sec-butyl, iso-butyl, t-butyl, and t-amyl. In preferred embodiments, the groups $R^1$, $R^2$ and $R^3$ are carefully selected so as to provide a coordination environment around the metal center such as to shield it to allow the complex to form as a volatile precursor. Additionally, $R^1$, $R^2$ and $R^3$ are also selected to permit a low melting point of the enolate complex.

In a preferred embodiment of the present invention, the groups $R^9$, $R^{10}R^{11}$ and $R^{12}$ of the dienolate anion of formula 2 are $C_4$-$C_6$ alkyl. In another embodiment of the present invention, $R^9$, $R^{10}R^{11}$ and $R^{12}$ are H or $C_1$-$C_6$ alkyl selected from the group consisting of: methyl, ethyl, iso-propyl, n-propyl, sec-butyl, iso-butyl, t-butyl, and t-amyl. In preferred embodiments, the groups $R^9$, $R^{10}R^{11}$ and $R^{12}$ are carefully selected so as to provide a coordination environment around the metal center such as to shield it to allow the complex to form as a volatile precursor. Additionally, $R^9$, $R^{10}R^{11}$ and $R^{12}$ are also selected to permit a low melting point of the dienolate complex.

In a preferred embodiment of the present invention, the groups $R^{13}$, $R^{14}$ and $R^{15}$ of the dienolate anion of formula 3 are $C_1$-$C_6$ alkyl. In another embodiment of the present invention, $R^{13}$, $R^{14}$ and $R^{15}$ are H or $C_1$-$C_6$ selected from the group consisting of: methyl, ethyl, iso-propyl, n-propyl, sec-butyl, iso-butyl, t-butyl, and t-amyl. In preferred embodiments the groups $R^{13}$, $R^{14}$ and $R^{15}$ are carefully selected so as to provide a coordination environment around the metal center, such as to shield it to allow the complex to form as a volatile precursor. Additionally, $R^{13}$, $R^{14}$ and $R^{15}$ are also selected to permit a low melting point of the dienolate complex.

In a preferred embodiment of the present invention, the groups $R^{16}$ and $R^{17}$ of the dienolate anion of Formula 4 are independently H or a $C_1$-$C_6$ alkyl group. In another embodiment of the present invention, $R^{16}$ and $R^{17}$ are each independently selected from the group consisting of: H, methyl, ethyl, iso-propyl, n-propyl, sec-butyl, iso-butyl, t-butyl, and t-amyl. In preferred embodiments, the groups $R^{16}$ and $R^{17}$ are carefully selected so as to provide a coordination environment around the metal center, such as to shield it to allow the complex to form as a volatile precursor. Additionally, $R^{16}$ and $R^{17}$ are also selected to permit a low melting point of the dienolate complex.

In a preferred embodiment of the present invention, the groups $R^{18}$, $R^{19}$, $R^{20}$ and $R^{21}$ of the dienolate anion of Formula 5 are H or $C_1$-$C_6$ alkyl. In another embodiment of the present invention, $R^{18}$, $R^{19}$, $R^{20}$ and $R^{21}$ are each independently selected from the group consisting of: H, methyl, ethyl, iso-propyl, n-propyl, sec-butyl, iso-butyl, t-butyl, and t-amyl. In preferred embodiments, the groups $R^{18}$, $R^{19}$, $R^{20}$ and $R^{21}$ are carefully selected so as to provide a coordination environment around the metal center, such as to shield it to allow the complex to form as a volatile precursor. Additionally, $R^{18}$, $R^{19}$, $R^{20}$ and $R^{21}$ are also selected to permit a low melting point of the dienolate complex.

The term "alkyl" as used herein includes linear, branched, or cyclic alkyl groups, comprising from 1 to 10 carbon atoms, from 1 to 6 carbon atoms, from 1 to 3 carbon atoms, from 3 to 5 carbon atoms, from 4 to 6 carbons atoms, or variations of the foregoing ranges. Exemplary alkyl groups include, but are not limited to, methyl, ethyl, n-propyl, isopropyl, n-butyl, isobutyl, sec-butyl, tert-butyl, tert-amyl, n-pentyl, n-hexyl, pentyl, isopentyl, tert-butyl and tert-amyl, 1,1-dimethylbutyl, cyclopentyl, and cyclohexyl. The term "alkyl" applies also to alkyl moieties contained in other groups, such as alkycyclopentadienyl, alkylpyrrolyl, alkylimidazolate, and alkylpyrazolate. The term "bulky" as used herein describes alkyl groups that are more sterically hindered compared to linear alkyl groups having the same number of carbon atoms and may include, for example, branched alkyl groups, cyclic alkyl groups, or alkyl groups having one or more side changes and/or substituents.

In preferred embodiments of the present invention, (L) shown in Formulae 1, 2, 3, 4, and 5 are selected from the group consisting of: amidinate, guanidinate, alkoxy, dialkylamide, diketonate, ketoiminate, diiminate, cyclopentadienyl, alkyl substituted cyclopentadienyl, alkoxy substituted cyclopentadienyl, amino substituted cyclopentadienyl, pyrrolyl, alkyl substituted pyrrolyl, alkoxy substituted pyrrolyl, and amino substituted pyrrolyl; alkyl substituted imidazoyl, alkoxy substituted imidazolate, aminosubsitituted imidazolate, pyrazolate or alkyl substituted pyrazolate.

In preferred embodiments of the present invention, the metal-containing precursor is a low melting solid or liquid. Exemplary melting point temperatures for the precursors disclosed herein include ranges having any one or more of the following endpoints: 100, 95, 90, 85, 80, 75, 70, 65, 60, 55, 50, 45, 40, 35, and/or 30° C. Examples of particular melting point ranges include, but are not limited to, 100° C. or less, 75° C. or less, or 60° C. or less.

In another embodiment of the present invention, the metal-containing precursors are represented by Structure A1:

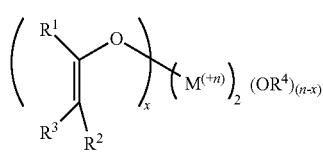

wherein M is a metal selected from the Lanthanides or from Group 3 to 16 of the Periodic Table. Preferably the metal M is selected from Group 4. In a preferred embodiment, M is selected from the group consisting of: Ti, Zr, and Hf. In a further preferred embodiment M is Ti. $R^1$, $R^2$ and $R^3$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, and tert-butyl. In a further preferred embodiment $R^1$ and $R^2$ are tert-butyl and (L) is alkoxide anion. An exemplary precursor of Structure A1 includes, but is not limited to: Bis(2,2,5,5-tetramethylhex-3-en-3-olato)bis(iso-propoxy)titanium. In another embodiment of the present invention, the metal-containing precursors are represented by Structure A2:

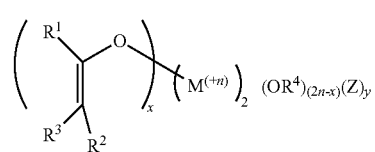

wherein M is a metal selected from the Lanthanides or from Group 3 to 16 of the Periodic Table. Preferably, the metal M is selected from Group 4. In a preferred embodiment, M is selected from the group consisting of: Ti, Zr, and Hf. In a further preferred embodiment M is Ti. $R^1$, $R^2$ and $R^3$ are selected independently from the group consisting of: hydrogen, methyl, ethyl, propyl, iso-propyl, butyl, isobutyl, sec-butyl, pentyl, isopentyl, sec-pentyl, hexyl, sec-hexyl, and tert-butyl. In a further preferred embodiment, $R^1$ and $R^2$ are tert-butyl and (L) is alkoxide. An exemplary precursor of Structure A2 includes, but is not limited to: bis(2,2,5,5-tetramethylhex-3-en-3-olato)hexa(ethoxy)di-titanium.

In another embodiment of the present invention, the metal-containing precursors are represented by Formula 1:

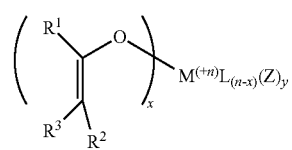

wherein M is a metal selected from the Lanthanides or from Group 3 to 16 of the Periodic Table. Preferably, the metal M is selected from Group 4. In a preferred embodiment, M is selected from the group consisting of: Ti, Zr, and Hf. In a further preferred embodiment, M is Ti. $R^1$, $R^2$ and $R^3$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, 1,1-dimethylbutyl, tert-butyl, and tert-amyl. In a further preferred embodiment, $R^1$ and $R^2$ are tert-butyl and (L) represents an amide anion. An exemplary precursor of Formula 1 includes, but is not limited to: tris(2,2,5,5-tetramethylhex-3-en-3-olato)(dimethylamido)titanium.

In another embodiment of the present invention, the metal-containing precursors are represented by Formula 2:

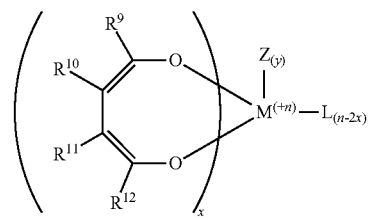

wherein M is a metal selected from the Lanthanides or from Group 3 to 16 of the Periodic Table. Preferably, the metal M is selected from Group 4. In a preferred embodiment, M is selected from the group consisting of: Ti, Zr, and Hf. In a further preferred embodiment, M is Ti. $R^1$, $R^2$ and $R^3$ are independently H or $C_1$-$C_6$ selected from the group consisting of: methyl, ethyl, propyl, iso-propyl, butyl, isobutyl, sec-butyl, pentyl, isopentyl, sec-pentyl, hexyl, sec-hexyl, tert-butyl, 1,1-dimethylbutyl, tert-butyl, and tert-amyl. In a further preferred embodiment, $R^9$ and $R^{12}$ are tert-butyl, $R^{19}$ and $R^{11}$ are hydrogen, and (Z) is an alkylamine. An exemplary precursor of Formula 2 includes, but is not limited to: bis(2,2,7,7-tetramethylocta-3,5-dien-3,6-diolato)bis(dimethylamino)titanium.

In another embodiment of the present invention, the metal-containing precursors are represented by Structure B, wherein M is a metal from Group 3 to Group 7 of the Periodic Table; $R^1$, $R^2$, $R^3$, and $R^5$ are independently H or $C_1$-$C_6$ selected from the group consisting methyl, ethyl, propyl, iso-propyl, and tert-butyl; n=3 to 6; and m=1 to 5.

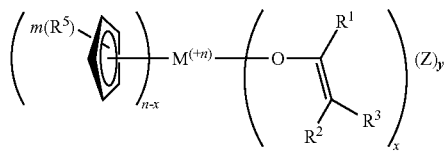

In preferred embodiments, M is selected from the group consisting of: Sc, La, V, Nb, Ta, Cr, Mo, W, Mn, Re, Ce, Pr, Sm, Eu, Gd, Tb, Dy, Ho, Er, Yb, Lu, Ti, Zr, and Hf. In other preferred embodiments, M is selected from the group consisting of: Sc, La, Ti, Zr, Hf, V, Nb, Ta, Cr, Mo, W, Mn, and Re.

Exemplary precursors of Structure B include, but not limited to,
methylcyclopentadienyltri(4,4-dimethylpent-2-en-3-olato) titanium,
methylcyclopentadienyltri(4,4-dimethylpent-2-en-3-olato) zirconium,
methylcyclopentadienyltri(4,4-dimethylpent-2-en-3-olato) hafnium,
ethylcyclopentadienyltri(4,4-dimethylpent-2-en-3-olato)titanium,
ethylcyclopentadienyltri(4,4-dimethylpent-2-en-3-olato)zirconium,
ethylcyclopentadienyltri(4,4-dimethylpent-2-en-3-olato) hafnium,
methylcyclopentadienyltri(2,2,5-dimethylpent-2-en-3-olato)titanium,
methylcyclopentadienyltri(2,2,5-trimethylhex-3-en-3-olato) zirconium,
methylcyclopentadienyltri(2,2,5-trimethylhex-3-en-3-olato) hafnium,
ethylcyclopentadienyltri(2,2,5-trimethylhex-3-en-3-olato)titanium,
ethylcyclopentadienyltri(2,2,5-trimethylhex-3-en-3-olato) zirconium,
ethylcyclopentadienyltri(2,2,5-trimethylhex-3-en-3-olato) hafnium,
methylcyclopentadienyltri(2,2,5,5-tetramethylhex-3-en-3-olato)titanium,
methylcyclopentadienyltri(2,2,5,5-tetramethylhex-3-en-3-olato)zirconium,
methylcyclopentadienyltri(2,2,5,5-tetramethylhex-3-en-3-olato)hafnium,
ethylcyclopentadienyltri(2,2,5,5-tetramethylhex-3-en-3-olato)titanium,
ethylcyclopentadienyltri(2,2,5,5-tetramethylhex-3-en-3-olato)zirconium, and
ethylcyclopentadienyltri(2,2,5,5-tetramethylhex-3-en-3-olato)hafnium.

In another embodiment of the present invention, the metal-containing precursors are represented by Structure C, wherein M is a metal selected from the lanthanides and Group 3 to Group 16 of the Periodic Table; $R^1$, $R^2$ and $R^3$ are independently H or $C_1$-$C_6$ selected from the group consisting of: methyl, ethyl, propyl, iso-propyl, butyl, sec-butyl, tert-butyl and tert-amyl; p=1, 2, 3, or 4; (n)=3, 4, 5, 6; and x=1, to 5.

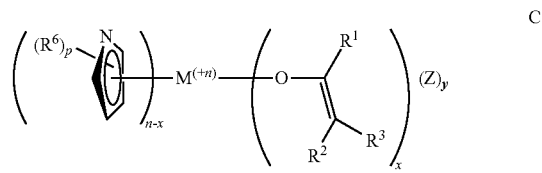

In preferred embodiments, M is selected from the group consisting of: Sc, La, V, Nb, Ta, Cr, Mo, W, Mn, Re, Ce, Pr, Sm, Eu, Gd, Tb, Dy, Ho, Er, Yb, Lu, Ti, Zr, and Hf. In one preferred embodiments, M is selected from the group consisting of: Sc, La, Ti, Zr, Hf, V, Nb, Ta, Cr, Mo, W, Mn, and Re. In more preferred embodiments of the present invention, M is selected from the group consisting of: La, Ce, Pr, Sm, Eu, Gd, Tb, Dy, Ho, Er, Yb, Lu, Ti, Zr, and Hf.

Features described in connection with one aspect of the invention can be used in combination with other aspects of the invention.

The method disclosed herein deposits metal-containing films using atomic layer deposition (ALD) or chemical vapor deposition (CVD) processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. In these embodiments, the deposition temperature may be relatively lower, or may range from 200° C. to 400° C., and may allow for a wider process window to control the specifications of film properties required in end-use applications. Exemplary deposition temperatures for the PEALD or PECCVD deposition include ranges having any one or more of the following endpoints: 200, 225, 250, 275, 300, 325, 350, 375, 400, 425, 450, 475, 500, 525, 550, 575, 600, 625, 650, 675 and/or 700° C.

In one embodiment of the method disclosed herein, a metal silicate or metal silicon oxynitride film is formed onto at least one surface of a substrate using a metal-containing precursor of Formulae 1, 2, 3, 4 or 5 of the present invention, a silicon-containing precursor, an oxygen source, and optionally a nitrogen source. Although metal-containing and silicon-containing precursors typically react in either liquid form or gas phase, thereby preventing film formation, the method disclosed herein avoids pre-reaction of the metal containing and silicon-containing precursors by using ALD or CCVD methods that separate the precursors prior to and/or during the introduction to the reactor. In this connection, deposition techniques, such as an ALD or CCVD processes, are used to deposit the metal-containing film.

For example, in certain embodiments, an ALD process is used to deposit the metal-containing film. In a typical ALD process, the film is deposited by exposing the substrate surface alternatively to the metal enolate, then the silicon-containing precursor or to the metal dienolate then the silicon-containing precursor. Film growth proceeds by self-limiting control of surface reaction, the pulse length of each precursor, and the deposition temperature. However, once the surface of the substrate is saturated, the film growth ceases. In yet another embodiment, the metal-containing film may be deposited using a CCVD process. In this embodiment, the CCVD process may be performed using a higher temperature range than the ALD window, or from 350° C. to 800° C. thereby preventing, for example, precursor decomposition. Exemplary deposition temperatures for the CCVD deposition include ranges having any one or more of the following endpoints (provided in degrees Celsius): 200, 225, 250, 275, 300, 325, 350, 375, 400, 425, 450, 475, 500, 525, 550, 575, 600, 625, 650, 675, 700, 725, 750, 775 and 800° C.

In certain embodiments, the method disclosed herein forms the metal oxide films using metal enolate or dienolate precursors and an oxygen source.

As mentioned previously, the method disclosed herein forms the metal-containing films using at least one metal precursor such as, for example, the metal-containing precursors having formula I described herein, optionally at least one silicon-containing precursor, optionally an oxygen source, optionally an additional metal-containing or other metal-containing precursor, optionally a reducing agent, and optionally a nitrogen source. Although the precursors and sources used herein may be sometimes described as "gaseous," it is understood that the precursors can be either liquid or solid which are transported with or without an inert gas into the reactor via direct vaporization, bubbling or sublimation. In some case, the vaporized precursors can pass through a plasma generator. Alternatively, the enolate and dienolate precursors described herein can also be dissolved in a solvent and the resulting solution flash evaporated by a Direct Liquid Injection (DLI) system to deliver precursor vapor to the CVD or ALD chamber.

In certain embodiments, other metal-containing precursors can be used in conjunction with the metal-containing precursors of the present invention. Metal commonly used in semiconductor fabrication include: titanium, tantalum, tungsten, hafnium, zirconium, cerium, zinc, thorium, bismuth, lanthanum, strontium, barium, lead, and combinations thereof. Examples of other precursors, containing these metals include, but are not limited to: tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, dibariun tetra(2,4,5-tri-tert-butylimidazolate), dibarium tetra(2-tert-butyl-4,5-di-tert-amylimidazolate), distrontiun tetra(2,4,5-tri-tert-butylimidazolate), distrontium tetra(2-tert-butyl-4,5-di-tert-amylimidazolate), $M(R_nC_5H_{5-n})_2$, wherein (n)=1 to 5 and R is selected from linear or branched $C_{1-6}$ alkyls; $M(R_nC_4NH_{4-n})_2$, wherein (n)=2 to 4, R is selected from linear or branched $C_{1-6}$ alkyls, and $M(R_nN_2H_{3-n})_2$, where (n)=2 to 3, R is selected from linear or branched $C_{1-6}$ alkyls, and combinations thereof.

In one embodiment, the metal-containing precursors, that can be used in addition to the Group 4 metal precursors described herein to provide a metal-containing film, are polydentate β-ketoiminates which are described, for example, in Applicants' co-pending application US2007/0248754A1, U.S. Ser. No. 11/945,678 filed on Nov. 27, 2007, Applicants' co-pending application U.S. Ser. No. 12/266,806 which was filed on Nov. 11, 2008 Applicants' patents U.S. Pat. No. 7,691,984, U.S. Pat. No. 7,723,493.

In embodiments wherein the metal film deposited is a metal silicate, the deposition process further involves the introduction of at least one silicon-containing precursor. Examples of suitable silicon-containing precursors include a monoalkylaminosilane precursor, a hydrazinosilane precursor, or combinations thereof.

In certain embodiments, the silicon-containing precursor comprises a monoalkylaminosilane precursor having at least one N—H fragment and at least one Si—H fragment. Suitable monoalkylaminosilane precursors containing both the N—H fragment and the Si—H fragment include, for example, bis(tert-butylamino)silane (BTBAS), tris(tert-butylamino)silane, bis(iso-propylamino)silane, tris(iso-propylamino)silane, and mixtures thereof.

In one embodiment, the monoalkylaminosilane precursor has the formula $(R^5NH)_n SiR^6_m H_{4-(n+m)}$ wherein $R^5$ and $R^6$ are the same or different and independently selected from the group consisting of alkyl, vinyl allyl, phenyl, cyclic alkyl, fluoroalkyl, and silylalkyl and wherein n is a number ranging from 1 to 3, m is a number ranging from 0 to 2, and the sum of "n+m" is a number that is less than or equal to 3.

In another embodiment, the silicon-containing precursor comprises a hydrazinosilane having the formula $(R^7_2N-NH)_x SiR^8_y H_{4-(x+y)}$ wherein $R^7$ and $R^8$ are same or different and independently selected from the group consisting of alkyl, vinyl, allyl, phenyl, cyclic alkyl, fluoroalkyl, silylalkyls and wherein x is a number ranging from 1 to 2, y is a number ranging from 0 to 2, and the sum of "x+y" is a number that is less than or equal to 3. Examples of suitable hydrazinosilane precursors include, but are not limited to, bis(1,1-dimethylhydrazino)-silane, tris(1,1-dimethylhydrazino)silane, bis(1,1-dimethylhydrazino)ethylsilane, bis(1,1-dimethylhydrazino)isopropylsilane, bis(1,1-dimethylhydrazino)vinylsilane, and mixtures thereof.

Depending upon the deposition method, in certain embodiments, the silicon-containing precursor may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds.

The silicon-containing precursors react with the metal hydroxyl groups formed by the reaction of the metal amide with the oxygen source and become chemically adsorbed onto the surface of the substrate which results in the formation of a silicon oxide or a silicon oxynitride via metal-oxygen-silicon and metal-oxygen-nitrogen-silicon linkages, thus providing the metal silicate or the metal silicon oxynitride film.

As previously mentioned, some of the films deposited using the methods described herein (e.g., metal silicate or the metal silicon oxynitride films) may be formed in the presence of oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $N_2O$, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 standard cubic centimeters per minute (sccm) or from about 1 to about 1000 sccm. The oxygen source can be introduced for a time that ranges from about 0.1 to about 100 seconds. In one particular embodiment, the oxygen source comprises water having a temperature of 10° C. or greater.

In this or other embodiments wherein the film is deposited by an ALD process, the precursor pulse can have a pulse duration that is greater than 0.01 seconds, and the oxidant pulse duration can have a pulse duration that is greater than 0.01 seconds, while the water pulse duration can have a pulse duration that is greater than 0.01 seconds. In yet another embodiment, the purge duration between the pulses that can be as low as 0 seconds.

The deposition methods disclosed herein may involve one or more purge gases. The purge gas, which is used to purge away unconsumed reactants and/or reaction byproducts, is an inert gas that does not react with the precursors and may preferably be selected from the group consisting of Ar, $N_2$, He, $H_2$ and mixture thereof. In certain embodiments, a purge gas such as Ar is supplied into the reactor at a flow rate ranging from about 10 to about 2000 sccm for about 0.1 to 1000 seconds, thereby purging the unreacted material and any byproduct that remain in the reactor.

In certain embodiments, such as, for example, for those embodiments where a metal silicon oxynitride film is deposited, an additional gas such as a nitrogen source gas may be introduced into the reactor. Examples of nitrogen source gases may include, for example, NO, $NO_2$, ammonia, hydrazine, monoalkylhydrazine, dialkylhydrazine, and combinations thereof.

In one embodiment of the method described herein, the temperature of the substrate in the reactor, i.e., a deposition chamber, is about 600° C. or below or about 500° C. or below or from 250 to 400° C. In this or other embodiments, the pressure may range from about 0.1 Torr (13 Pa) to about 100 Torr (13 kPa) or from about 0.1 Torr (13 Pa) to about 5 Torr (670 Pa).

The respective step of supplying the precursors, the oxygen source, and/or other precursors or source gases may be performed by changing the time for supplying them to modify the stoichiometric composition of the resulting metal silicate, metal silicon oxynitride film, or other metal-containing film.

Energy is applied to the at least one of the precursor, oxygen source gas, reducing agent, or combination thereof to induce reaction and to form the metal-containing film on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

In yet another embodiment of the method disclosed herein, the metal-containing film is formed using a vapor deposition method that comprises the steps of: a. introducing a metal-containing precursor of Formula I, 2, 3, 4 or 5 in a vapor state into a reaction chamber and chemisorbing the metal-containing precursor onto a substrate which is heated; b. purging away the unreacted metal-containing precursor; c. introducing an oxygen source onto the heated substrate to react with the adsorbed metal-containing precursor; and d. purging away the unreacted oxygen source. The above steps define one cycle for the method described herein; and the cycle can be repeated until the desired thickness of a metal-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to modify the stoichiometric composition of the resulting metal oxide film. For multicomponent metal oxide films, a strontium-containing precursor, a barium-containing precursor or both precursors can be alternately introduced in step a into the reactor chamber to deliver the elements of barium and strontium for film, such as barium strontium titanate (BST).

The metal-containing precursor of the present invention or the metal-containing precursor of the present invention in conjunction with other metal containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Mn, to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD or ALD process.

In one embodiment of the method described herein, a cyclic deposition process, such as CCVD, ALD, or PEALD, may be employed, wherein a metal-containing precursor of the present invention or its solution and an oxygen source such as, for example, ozone, oxygen plasma or water plasma are employed. The gas lines connecting from the precursor canisters to the reaction chamber are heated to one or more temperatures ranging from about 150° C. to about 200° C. depending upon the process requirements, and the container of the metal-containing precursor is kept at one or more temperatures ranging from about 100° C. to about 190° C. for bubbling whereas the solution comprising the metal-containing precursor is injected into a vaporizer kept at one or more temperatures ranging from about 150° C. to about 180° C. for direct liquid injection. A flow of 100 sccm of argon gas may be employed as a carrier gas to help deliver the vapor of the metal-containing precursor to the reaction chamber during the precursor pulsing. The reaction chamber process pressure is about 1 Torr (13 Pa). In a typical ALD or CCVD process, the substrate such as silicon oxide or metal nitride are heated on a heater stage in a reaction chamber that is exposed to the metal-containing precursor initially to allow the complex to chemically adsorb onto the surface of the substrate. An inert gas, such as argon gas, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors of the present invention may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate. The solvent employed in solubilizing the precursor for use in a deposition process may comprise any compatible solvent or their mixture including aliphatic hydrocarbons (e.g., hexane, heptane, octane, and pentane), aromatic hydrocarbons (e.g., benzene or toluene), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like. Further examples of suitable solvent are selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines and organic amides.

Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

The utility of specific solvent compositions for particular precursors may be readily empirically determined, to select an appropriate single component or multiple component solvent medium for the liquid delivery vaporization and transport of the specific metal-enolate precursor that is employed.

In another embodiment, a direct liquid delivery method can be employed by dissolving the metal-containing precursor of the present invention in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, amines, polyamines, and organic amides, preferably a solvent with a high boiling point, such as mesitylene (b.p. 164° C.) or N-methyl-2-pyrrolidinone (b.p. 202° C.).

The method described herein also includes a cyclic deposition process for the formation of ternary metal oxide films wherein a plurality of precursors are sequentially introduced into a deposition chamber, vaporized and deposited on a substrate under conditions for forming a said ternary metal oxide film.

In one particular embodiment, the resultant metal oxide films can be exposed to a post-deposition treatment such as a plasma treatment to densify the film.

As mentioned previously, the method described herein may be used to deposit a metal-containing film on at least a portion of a substrate. Examples of suitable substrates include but are not limited to, semiconductor materials such as strontium titanate, barium strontium titanate, yttrium oxide doped with titanium, lanthanum oxide doped with titanium, and other lanthanide oxides doped with titanium.

EXAMPLES

In the following examples, the GCMS Spectra for the examples were performed on a Hewlett Packard 5890 Series 11 GC and 5972 series mass selective detector with a HP-5MS. The NMR analyses for the examples were obtained on a Bruker AMX 500 spectrometer operating at 500.MHz. Chemical shifts were set from $C_6D_6$ at 7.16 ppm in $^1H$ and 128.39 parts per million (ppm) in $^{13}C$.

Example 1

Synthesis of bis(2,2,5,5-tetramethylhex-3-en-3-olato) hexa(ethoxy)di-titanium

Under a nitrogen atmosphere, 16 ml of 2.5M nBuLi (0.04 moles) were added dropwise to 4.04 g (0.04 moles) of diisopropylamine in 50 ml of dry teytrahydrofuran cooled to −60° C. using dry ice. After 30 minutes at −60° C., the mixture was allowed to warm to room temperature for 20 minutes then cooled back to −60° C. 6.24 g (0.04 moles) of 2,2,5,5-tetramethylhexan-3-one dissolved in 80 ml of tetrahydrofuran were then added dropwise over a 30 minute period, maintaining −60° C. The mixture was maintained at −60° C. for an additional 45 minutes then allowed to warm to room temperature over a 20 minute period. The resulting lithium enolate was then added over a 20 minute period to 8.72 g (0.04 moles) of tris(ethoxy)monochloro titanium dissolved in 50 ml of tetrahydrofuran at −60° C. The reaction mixture was then allowed to warm to room temperature overnight. The solvents were then removed by vacuum, 250 ml of dry hexane were added to the resulting crude reaction product, the mixture agitated then filtered and the hexane removed resulting in a orange-yellow solid. This product was then vacuum distilled at 120° C. to give 10.7 g (80% yield) of di-titanium bis(2,2,5,5-tetramethylhex-3-en-3-olato)hexa(ethoxy), characterized by X-ray diffraction, shown in FIG. 1.

Example 2

Synthesis of Bis(2,2,5,5-tetramethylhex-3-en-3-olato)bis(iso-propoxy)titanium

Figure 2:
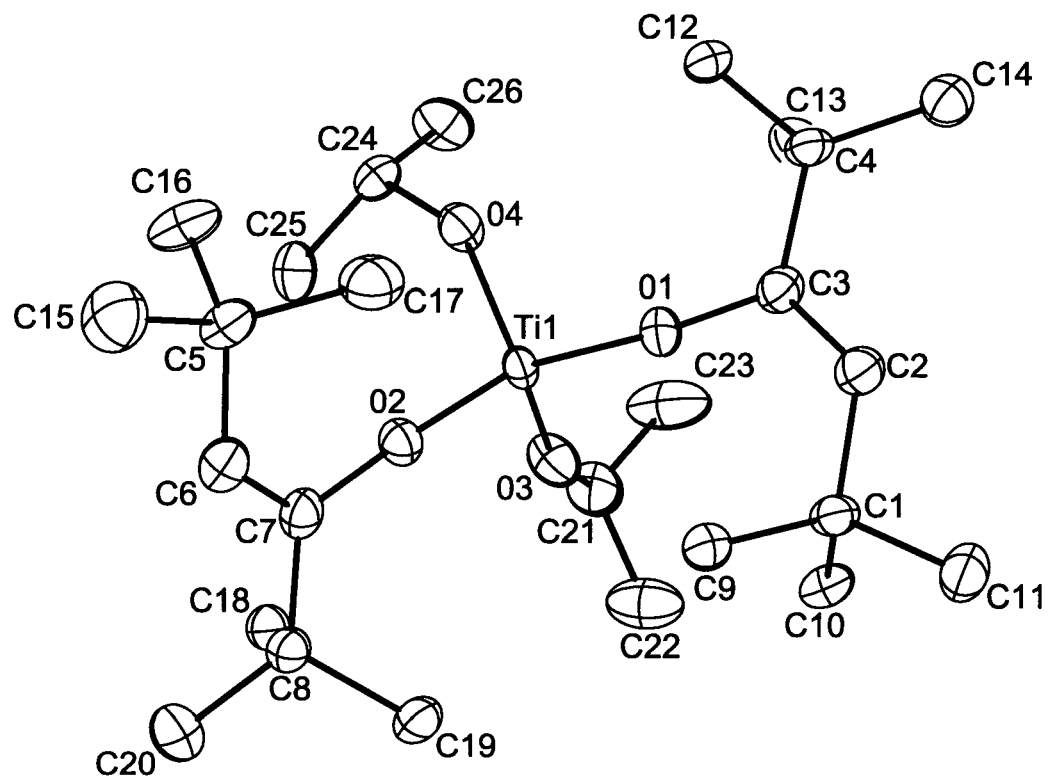
FIG. 2 is a schematic representation of a crystal structure of bis(2,2,5,5-tetramethylhex-3-en-3-olato)bis(iso-propoxy)titanium, characterized by X-ray single crystal diffraction.
Figure 3:
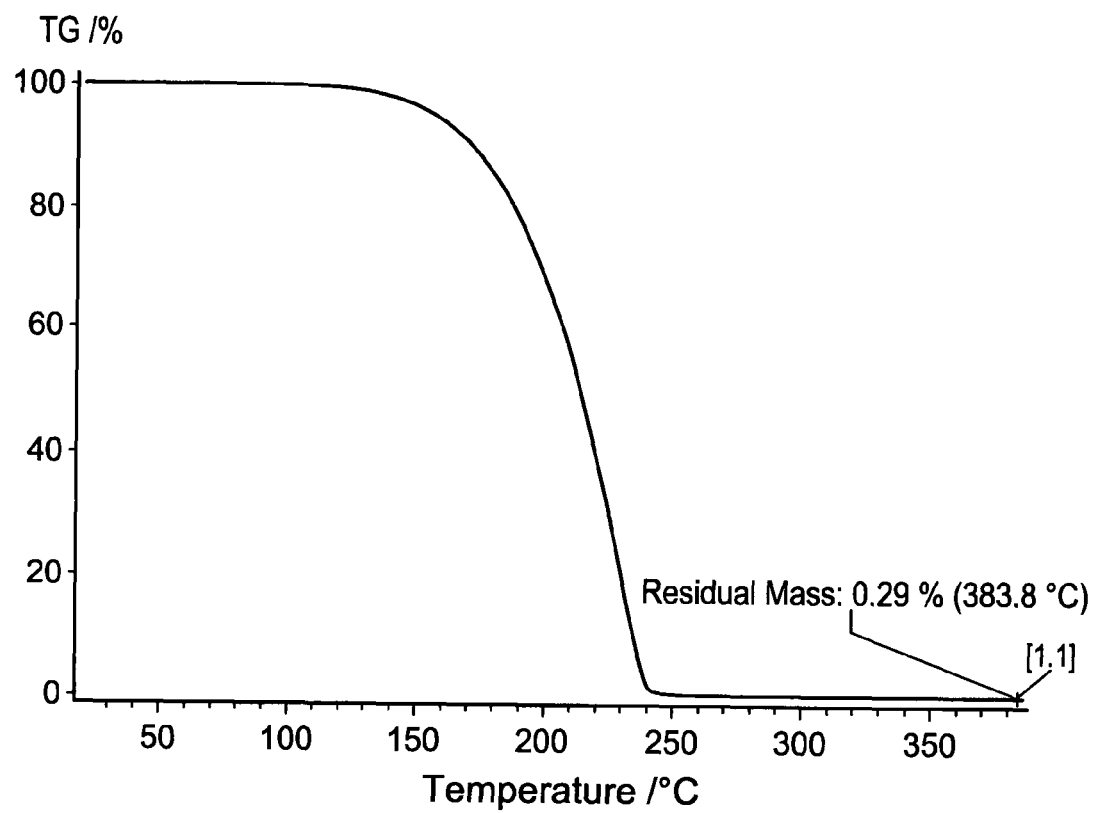
FIG. 3 is a graph of a thermogravimetric analysis (TGA) of bis(2,2,5,5-tetramethylhex-3-en-3-olato)(bis(iso-propoxy) titanium.

Under a nitrogen atmosphere, 16 ml of 2.5M nBuLi (0.04 moles) were added dropwise to 4.04 g (0.04 moles) of diisopropylamine in 50 ml of dry teytrahydrofuran cooled to −60° C. using dry ice. After 30 minutes at −60 C, the mixture was allowed to warm to room temperature for 20 minutes then cooled back to −60° C. 6.24 g (0.04 moles) of 2,2,5,5-tetramethylhexan-3-one dissolved in 80 ml of tetrahydrofuran were then added dropwise over a 30 minute period, maintaining −60° C. The mixture was maintained at −60° C. for an additional 45 minutes then allowed to warm to room temperature over a 20 minute period. The resulting lithium enolate was then added over a 20 minute period to 10.4 g (0.04 moles) of tris(isopropoxy)monochloro titanium dissolved in 50 ml of tetrahydrofuran at −60° C. The reaction mixture was then allowed to warm to room temperature and then brought to reflux overnight. The solvents were then removed by vacuum, 250 ml of dry hexane were added to the resulting crude reaction product, the mixture agitated then filtered and the hexane removed resulting in a orange-yellow solid. This product was then vacuum distilled at 120° C. to give 11.1 g of crude product. This was redistilled under vacuum up to 115° C. The product that did not distill over was allowed to cool, forming a crystalline solid, melting point 34° C., structure proven by X-ray analysis, shown as FIG. 2. TGA shows (FIG. 3) it is volatile, leaving an involatile residue of only 0.29% indicating and can be used as a titanium source in a CVD/ALD process.

Example 3

Tris(2,2,5,5-tetramethylhex-3-en-3-olato)(dimethylamido)titanium

Figure 4:
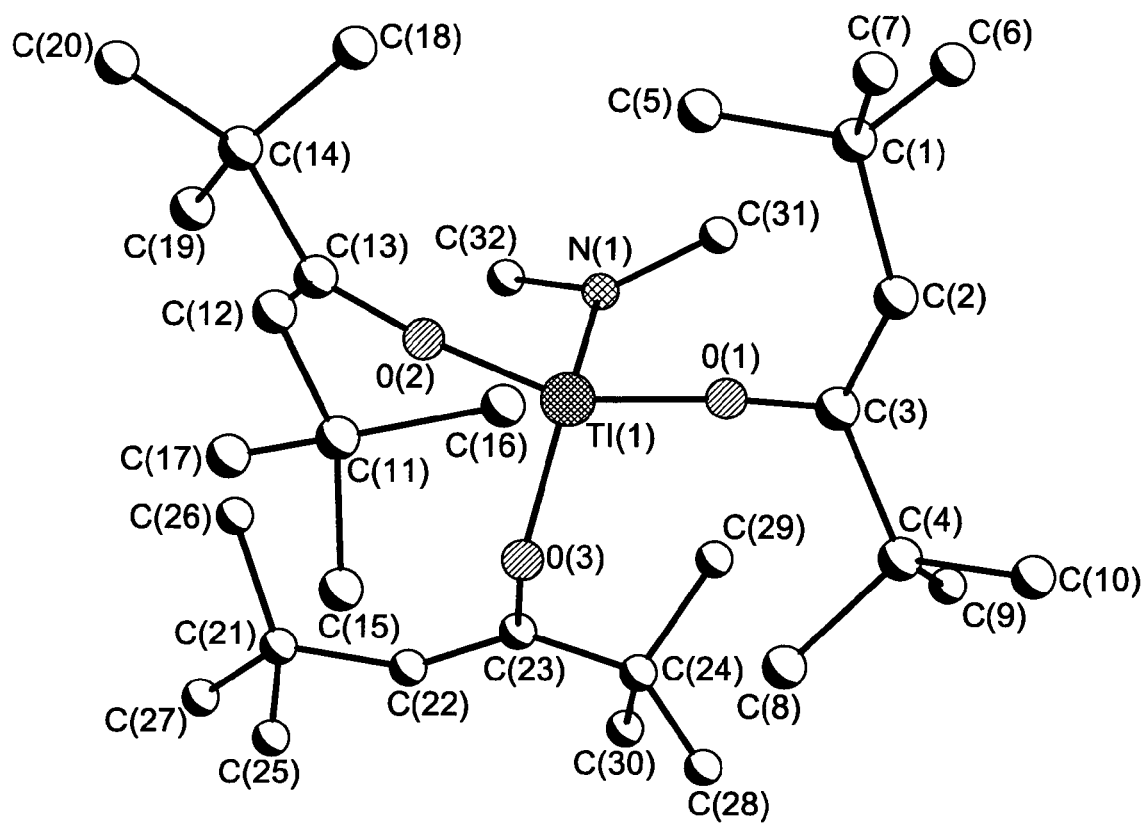
FIG. 4 is a schematic representation of a crystal structure of tris(2,2,5,5-tetramethylhex-3-en-3-olato)(dimethylamido)titanium.
Figure 5:
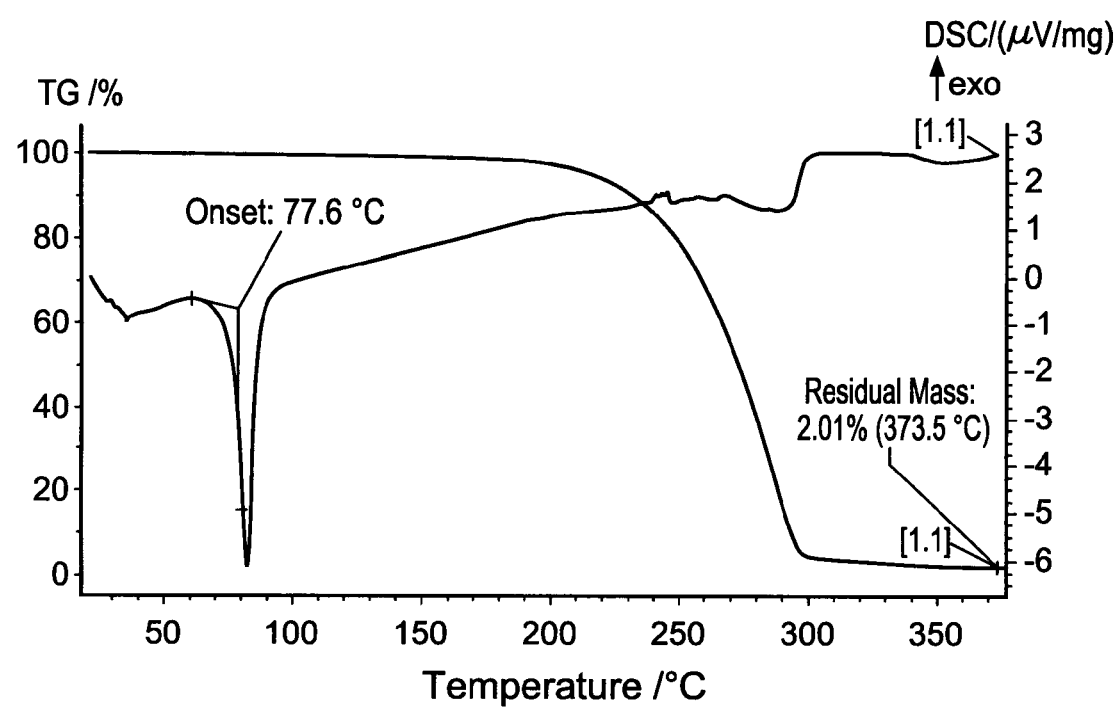
FIG. 5 is a graph of a thermogravimetric analysis (TGA) of tris(2,2,5,5-tetramethylhex-3-en-3-olato)(dimethylamido)titanium.

Under a nitrogen atmosphere, 25.6 ml of 2.5M nBuLi (0.064 moles) were added dropwise to 9.0 ml (0.064 moles) of diisopropylamine in 75 ml of dry teytrahydrofuran cooled to −60° C. using dry ice. After 30 minutes at −60 C, the mixture was allowed to warm to room temperature for 20 minutes then cooled back to −60° C. 10.0 g (0.064 moles) of 2,2,5,5-tetramethylhexan-3-one dissolved in 125 ml of tetrahydrofuran were then added dropwise over a 30 minute period, maintaining −60° C. The mixture was maintained at −60° C. for an additional 45 minutes then allowed to warm to room temperature over a 20 minute period. The resulting lithium enolate was then slowly added to 2.34 ml (0.021 moles) of titanium tetrachloride stirred in 75 ml of dry tetrahydrofuran. The resulting mixture was then refluxed overnight. The mixture was then allowed to cool to room temperature and 1.1 g (0.021 moles) of lithium dimethylamide added as 21.8 g of a 5 wt % suspension in hexane and the resulting mixture refluxed overnight. The solvents were removed by vacuum. 250 ml of dry hexane were added to the resulting crude reaction product, the mixture agitated then filtered and the hexane removed resulting in 11.6 g of an orange brown oil. This was then vacuum distilled at 100 mTorr (13 Pa) at 180° C. to yield the final product as a waxy orange solid, melting point 77.3° C., yield 8.5 g (71%). TGA showed an involatile residue of only 2.01%. The combination of low melting point and low TGA residue indicate this complex is an excellent titanium source for ALD or CVD. $^1$H NMR: (500 MHz, $d_8$ toluene): δ=1.24 (s, 27H), δ=1.32 (s, 27H), δ=3.27 (s, 6H), δ=4.45 (s, 3H). Structure proven by X-ray analysis of crystals grown from hexane, see FIG. 4.

Example 4

Bis(2,2,7,7-tetramethylocta-3,5-dien-3,6-diolato)bis(dimethylamino)titanium

Figure 6:
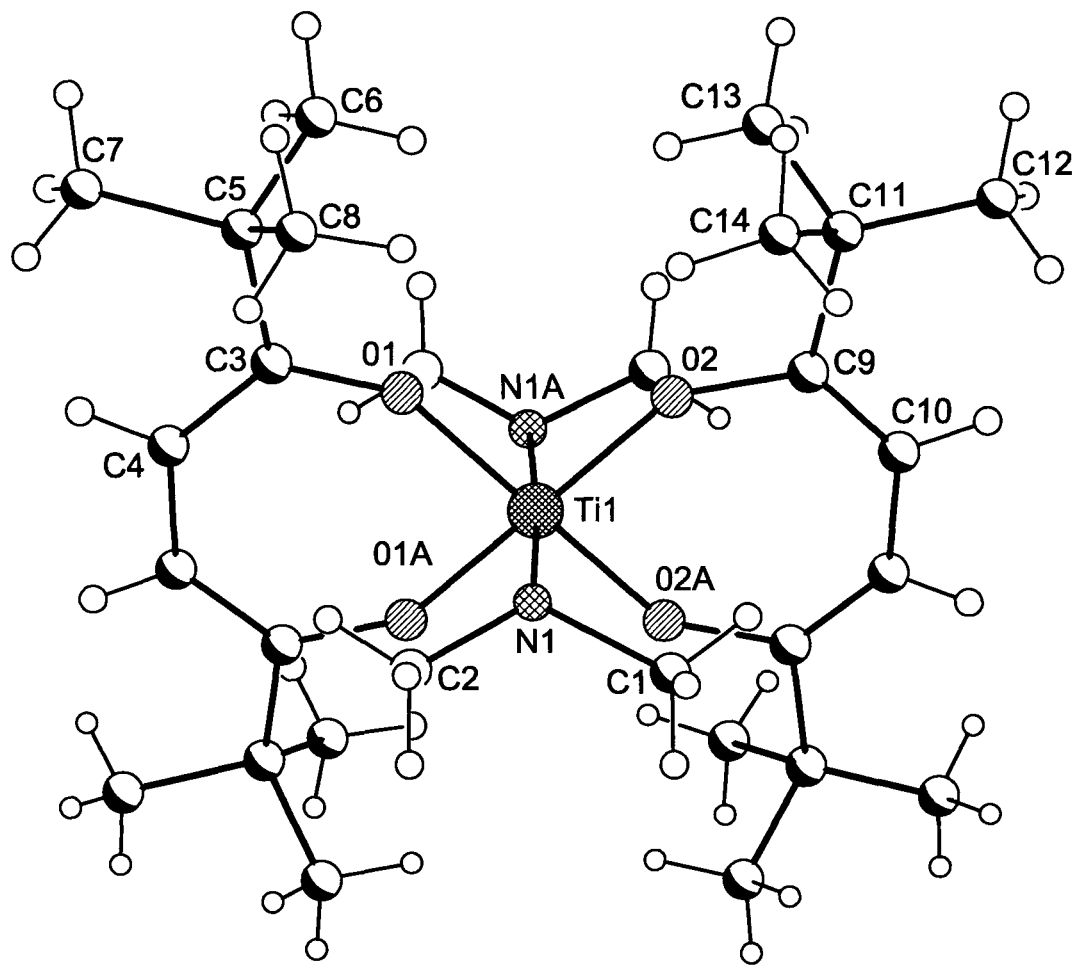
FIG. 6 is a schematic representation of a crystal structure of bis(2,2,7,7-tetramethylocta-3,5-diene-3,6-diolato)bis(dimethylamino)titanium.

Under a nitrogen atmosphere, 14.6 ml of 2.5M nBuLi (0.0364 moles) were added dropwise to 8.4 ml (0.04 moles) of hexamethyldisilazane in 100 ml of dry hexane cooled to 0° C. using ice. After 15 minutes 3.25 g (0.0164 moles) of 2,2,7,7-tetramethyl-3,6-octanedione were added dropwise over a 5 minute period leading to the formation of a precipitate of lithium dienolate. The resulting mixture was stirred an additional 15 minutes and then filtered and the solid rinsed with 2×20 ml of dry hexane after which it was dried by vacuum and dissolved in 25 ml of tetrahydrofuran. A suspension of 37 g of 5 wt % of lithium dimethylamide (0.0364 moles) in hexane was then hydrolyzed by the slow addition of 0.6 g (0.0364 moles) of water in 5 ml of tetrahydrofuran. After stirring for 15 minutes the solvent and liberated dimethylamine were condensed under vacuum into a dry flask containing 3.03 g (0.0364 moles) of titanium tetrachloride bis(tetrahydrofuran) in 25 ml of tetrahydrofuran. This mixture was then stirred and the tetrahydrofuran solution of the lithium dienolate was slowly added at room temperature resulting in a brilliant deep mauve solution which was then stirred for 2 days at room temperature. The solvents were then removed by vacuum and the resulting dark mauve solid was extracted with hexane (500 ml total). Hexane was then removed by vacuum to yield a dark mauve solid, yield 1.4 g (32%). $^1$H NMR: (500 MHz, $d_8$ toluene): δ=1.38 (s, 36H), δ=1.76 (m, 2H), δ=1.95 (d, 12H), δ=5.23 (s, 4H). Structure proven by X-ray crystallography, see FIG. 6

Example 5 (Prophetic)

ALD of titanium dioxide using bis(2,2,5,5-tetramethylhex-3-en-3-olato)hexa(ethoxy)di-titanium The precursor bis(2,2,5,5-tetramethylhex-3-en-3-olato)hexa(ethoxy)di-titanium is delivered by pulse bubbling at 100° C. into an ALD reactor at a chamber pressure of 1 Torr (130 Pa). Oxidation pulses are provided by ozone from an ozone generator. Using silicon substrates at 300° C., 100 cycles of precursor/argon purge/ozone/argon purge results in the deposition of a titanium dioxide film.

Example 6 (Prophetic)

ALD of titanium dioxide using bis(2,2,5,5-tetramethylhex-3-en-3-olato)bis(iso-propoxy)titanium The precursor bis(2,2,5,5-tetramethylhex-3-en-3-olato)bis(iso-propoxy)titanium is delivered by pulse bubbling at 100° C. into an ALD reactor at a chamber pressure of 1 Torr (130 Pa). Oxidation pulses are provided by ozone from an ozone generator. Using silicon substrates at 300° C., 100 cycles of precursor/argon purge/ozone/argon purge results in the deposition of a titanium dioxide film.

Example 7 (Prophetic)

ALD of titanium dioxide using tris(2,2,5,5-tetramethylhex-3-en-3-olato)(dimethylamido)titanium The precursor tris(2,2,5,5-tetramethylhex-3-en-3-olato)(dimethylamido)titanium is delivered by pulse bubbling at 100° C. into an ALD reactor at a chamber pressure of 1 Torr (130 Pa). Oxidation pulses are provided by ozone from an ozone generator. Using silicon substrates at 300° C., 100 cycles of precursor/argon purge/ozone/argon purge results in the deposition of a titanium dioxide film.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims.

The invention claimed is:

1. A metal-containing precursor comprising an enolate ligand, said metal-containing precursor represented by the following Formula 1:

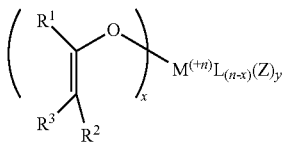

wherein M is a metal with an oxidation state of (n), from +2 to +6, selected from the Lanthanides or Group 3 to Group 16, of the Periodic Table; $R^1$, $R^2$ and $R^3$ are independently selected from the group consisting of: methyl, ethyl, propyl, iso-propyl, butyl, isobutyl, sec-butyl, pentyl, isopentyl, sec-pentyl, hexyl, sec-hexyl, tert-butyl, tert-amyl, and 1,1-dimethylbutyl; (L) is an anionic ligand or a mixture of anionic ligands selected from the group consisting of: alkoxy, alkylamino, and dialkylamino; (Z) is a neutral coordinating ligand selected from the group consisting of an alkylamine, polyalkylamine, ether, polyether, imidazole, pyridine, alkyl substituted pyridine, pyrimidine, alkyl substituted pyrimidine, and oxazole; (y)=0 to 4; (x)=1 to 6.

2. The precursor of claim 1 comprising bis(2,2,5,5-tetramethylhex-3-en-3-olato)bis(iso-propoxy)titanium.

3. The precursor of claim 1 comprising a compound from Formula 1, wherein (L) is an alkoxy anion, as represented by structure A1:

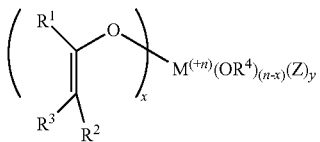

A1 wherein $R^4$ is selected from the group consisting of methyl, ethyl, propyl, isopropyl, butyl, isobutyl, sec-butyl, pentyl, isopentyl, sec-pentyl, hexyl, sec-hexyl, tert-butyl, tert-amyl, and 1,1-dimethylbutyl.

4. A method for forming a metal-containing film by a vapor deposition, the method comprising the steps of:
   a. introducing a metal-containing precursor of claim 1 in a vapor state into a reaction chamber and chemisorbing the metal-containing precursor onto a substrate which is heated;
   b. purging away the unreacted metal-containing precursor;
   c. introducing an oxygen source onto the heated substrate to react with the sorbed metal-containing precursor; and
   d. purging away the unreacted oxygen source.

5. A method of claim 4 wherein the vapor deposition method comprises chemical vapor deposition.

6. A method of claim 5 wherein the vapor deposition method comprises plasma enhanced chemical vapor deposition.

7. A method of claim 4 wherein the vapor deposition method comprises atomic vapor deposition.

8. A method for forming a metal-containing film by an atomic layer deposition method, the method comprising the steps of:
   a. introducing a metal-containing precursor of claim 1 in a vapor state into a reaction chamber and chemisorbing the metal-containing precursor onto a heated substrate;
   b. purging away the unreacted metal-containing precursor;
   c. introducing an oxidizing source selected from the group consisting of oxygen, ozone, nitrous oxide or water onto the heated substrate to react with the adsorbed metal-containing precursor; and,
   d. purging away the unreacted oxidizing source; and,
   repeating steps a through d to provide the metal-containing film.

* * * * *